United States Patent [19]

Yong et al.

[11] 4,412,007
[45] Oct. 25, 1983

[54] RAPID METHOD FOR BITUMEN ANALYSIS

[75] Inventors: Raymond N. Yong, Beaconsfield; Amar J. Sethi, Quebec, both of Canada

[73] Assignee: Suncor, Inc., Toronto, Canada

[21] Appl. No.: 340,946

[22] Filed: Jan. 20, 1982

[51] Int. Cl.³ ............................................. G01N 33/24
[52] U.S. Cl. ...................................... 436/139; 436/72; 436/163
[58] Field of Search .......... 23/230 R, 230 M, 230 EP, 23/230 HC; 436/60, 79, 75, 163, 139, 72

[56] References Cited

U.S. PATENT DOCUMENTS 3,273,967  9/1966  Wilson ........................... 23/230 EP
3,607,078  9/1971  Dietert et al. ..................... 23/230 R
3,836,330  9/1974  Melachrinos ..................... 23/230 R

OTHER PUBLICATIONS

Richards, U.S. Dept. of Agriculture Handbook No. 60, Feb. 1954, pp. 105–106.
Czarnecka et al., Chemical Abstracts, No. 93: 188861d, vol. 93, 1980.
Patel, Analytical Chemistry, vol. 46, No. 6, May 1974, pp. 794–795.

Primary Examiner—Arnold Turk
Attorney, Agent, or Firm—Paul Lipsitz

[57] ABSTRACT

Bitumen content of tailings or sludge obtained from processing of tar sands is quickly determined by a two step process wherein (1) clay mineral content is determined by adsorption of methylene blue and this value correlated to adsorbed organic material, (2) the content of total organic material is determined by a chromic acid oxidation, and the difference in these values gives the bitumen content.

3 Claims, 3 Drawing Figures

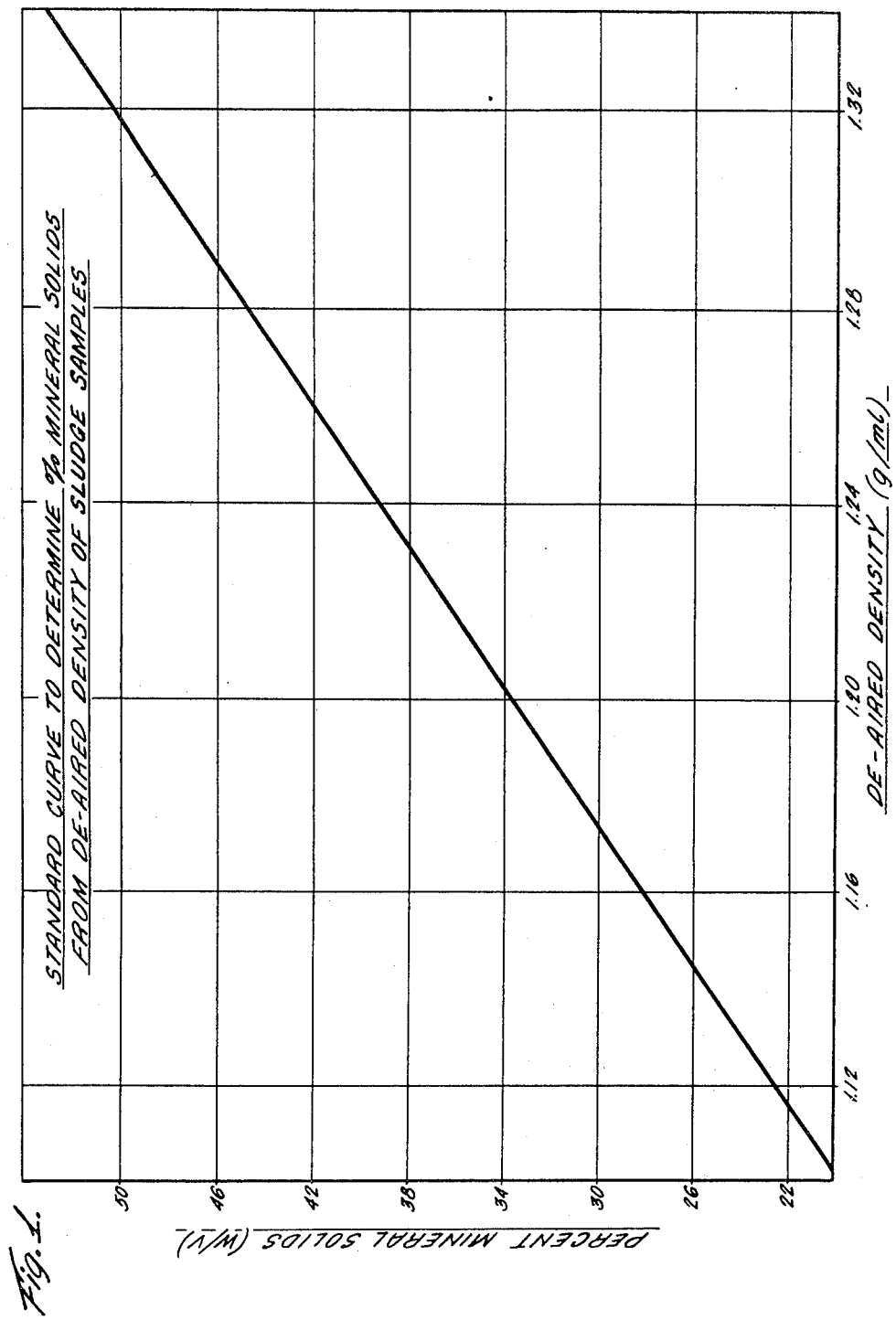

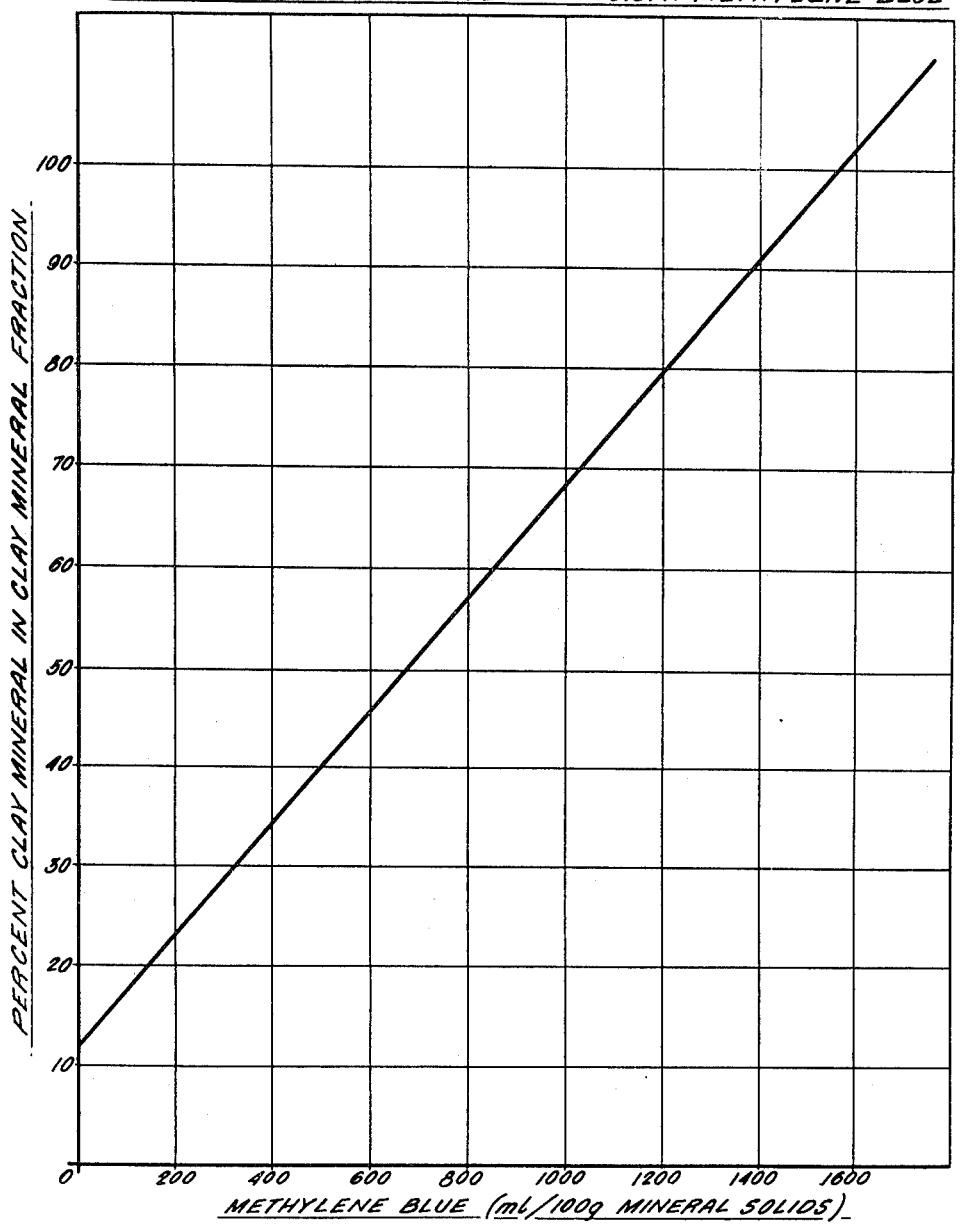
Fig. 2. STANDARD CURVE TO DETERMINE % CLAY MINERALS BY TITRATION OF SLUDGE WITH 0.01N METHYLENE BLUE

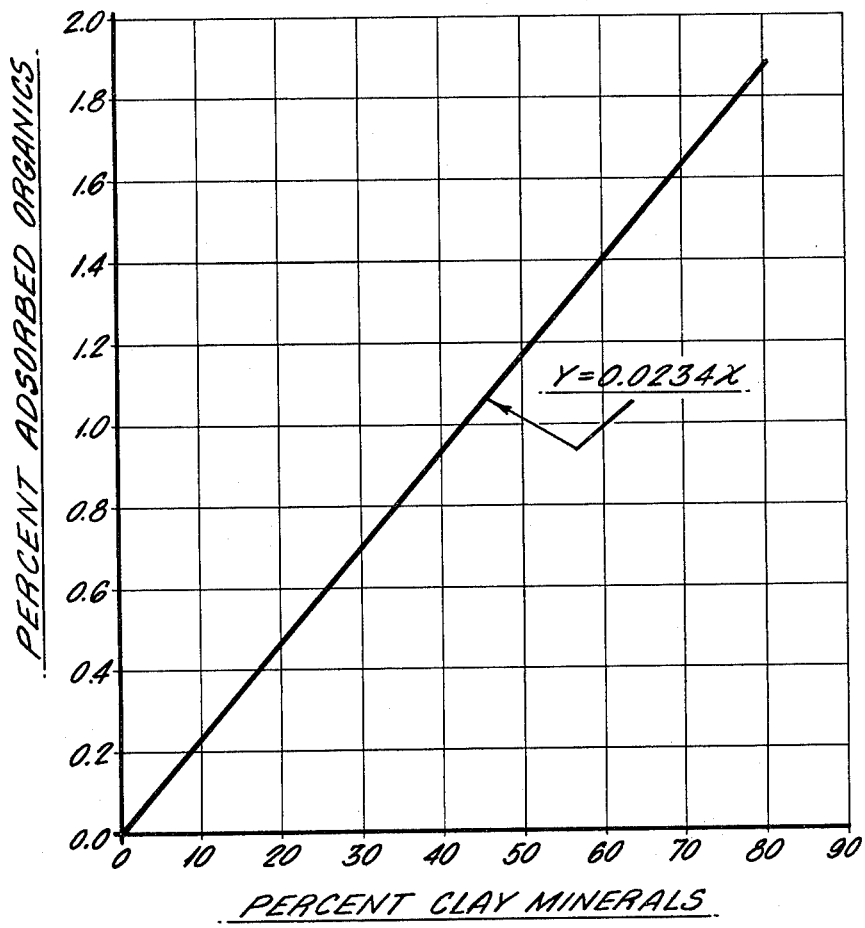

RAPID METHOD FOR BITUMEN ANALYSIS

BACKGROUND OF THE INVENTION

This invention relates to a method for the rapid determination of bitumen in the sludge generated by extraction of hydrocarbon oil from tar sands and similar materials.

Bitumen determinations are conventionally made only after lengthy laboratory procedures requiring at least 48 hours. These procedures include a technique of drying the sludge overnight, grinding, weighing, extracting with a mixture of carbon bisulfide, acetone, and methanol or other solvents in a soxhlet extractor, drying and a final weighing. While such a method gives good results it is a very long and tedious procedure. In tar processing plants it is important that bitumen analyses be made as quickly as possible in order that no holdup of sludge treatment occur. This invention provides such a rapid method.

SUMMARY OF THE INVENTION

In accord with the method of the invention, an analysis of the sludge to determine both clay mineral content and total organic content is made; the clay mineral content is used as a basis to determine organics adsorbed by clay minerals and this value is then subtracted from the total organics present as determined by a chromic acid oxidation. The analyses are easily made by titration techniques enabling the entire procedure to be completed in about one hour.

BRIEF DESCRIPTION OF THE DRAWINGS

FIG. 1 shows a curve for the relationship of minerals content to de-aired density.

FIG. 2 is a curve used for determination of clay minerals by methylene blue titration.

FIG. 3 is a curve showing the correlation of adsorbed organic materials from clay minerals.

DETAILED DESCRIPTION

The first step of the two step method, as indicated, involves the determination of the clay minerals content of the tailings or sludge resulting from the extraction of bitumen from tar sands and similar materials and is disclosed in Canadian application Ser. No. 365,173 filed Nov. 21, 1980 and U.S. application Ser. No. 312,606 filed Oct. 19, 1981, which disclosure is hereby incorporated by reference. The value of clay mineral content obtained by this method is converted to adsorbed organics by multiplying the clay minerals content by 0.0234 as shown by FIG. 3.

The second step of the invention is an oxidation of the sludge with chromic acid to obtain the amount of total organics present and this is done by titration with an appropriate indicator such as Ferroin. Other indicators may be used, but tests with diphenylamine as indicator are much less accurate.

The test methods are as follows:

Step I

Determination of Organics Adsorbed by Clay Minerals in Sludge

A known weight of sludge or tailings (5±1 g) is taken, dispersed in about 50 ml water and acidified with 2 ml of 10% $H_2SO_4$. This solution is titrated in 1 ml increments to the end point with methylene blue dye (0.01 N). The end point is reached when the sample has adsorbed all the dye possible, and the excess passes into the water solution. This point is visualized by placing a drop of the sludge suspension on filter paper by means of the blunt end of a 1 ml pipette. Before the excess is reached, a blue dot is formed, surrounded by a wet, colorless, circular area. When an excess of dye is attained, the blue color begins to extend into the wet area. The excess must remain after two minutes of shaking the titrated sample to ensure complete adsorption.

In order to establish empirical curves with which to correlate the methylene blue titration with clay mineral content, a direct determination of percent clay mineral is made by X-ray diffraction techniques with the particular type of sludge to be analyzed. In order to estimate the clay minerals in the tailings or sludge it is necessary to first establish their minerals content and relate this to deaired density. FIG. 1 shows such a curve where actual mineral content was obtained by the oven drying technique. The procedure for obtaining de-aired solids and preparing the empirical curves for the methylene blue titration as adsorbed organics follows:

1. The exact volume of a 25-ml pycnometer is determined by weighing empty and filled with distilled water.
2. A sample sludge is deaired under vacuum (74 cm Hg) for one hour.
3. The deaired sludge is carefully poured into the pycnometer and weighted—thus the weight and volume of the sludge are known.
4. The density is calculated:

density = [weight (g)/volume (ml)]

5. From the relationship of deaired density to percent mineral solids (w/v) given in FIG. 1, the amount of mineral solids in the sludge sample is found. The slope of this linear relationship may be somewhat different than theoretically expected, because of the presence of small amounts of dissolved or free gases still retained in the samples, even after deairing.
6. Several samples of a known volume or weight of sludge are taken to contain approximately 1–2 g mineral solids (as determined in step 5), acidified and titrated with methylene blue as described above.
7. The amount of clay minerals as determined by the x-ray diffraction technique versus the amount of methylene blue used may be plotted to obtain FIG. 2. These correlation curves are plotted from the analysis of numerous tailings and sludge samples. About 200 samples were analyzed to obtain the data in FIG. 2.
8. Samples with unknown content of clay or clay minerals may then be titrated with methylene blue and the clay mineral content obtained from the curves.
9. A known weight of mineral solids obtained after soxhlet extraction of an oven dried sample of the sludge is treated with hydrogen peroxide and heated to oxidize the adsorbed organics. The percent adsorbed organics is obtained from the weight loss of the treated sample and the percent adsorbed organics is plotted against percent clay minerals to obtain an empirical correlation, as shown in FIG. 3.

Step II

Determination of Total Organics by Chromate Oxidation

This method is disclosed in the text "Diagnosis And Improvement of Saline Alkaline Soils," U.S. Dept. of Agriculture Handbook N.Y. 60, February 1954, L. A. Richards, Editor, pages 105–106, which is hereby incorporated by reference.

Organic Determination with the Ferroin Indicator

A. Preparation of Solutions

1. Ferrous Sulfate 0.5 N: dissolve 140 g $FeSO_4.7H_2O$ in 500 mls distilled water. Then add 15 mls concentrated sulfuric acid, and dilute to 1 liter.
2. Potassium Dichromate 1.0 N: dilute 49.04 g $K_2Cr_2O_7$ to 1 liter with distilled water.
3. Ferroin indicator: dissolve 0.495 g indicator in 100 mls distilled water.

B. Test Procedure

Weigh about 0.3 g sludge into a 500 ml Erlenmyer flask. Pipette 20 mls 1 N $K_2Cr_2O_7$ into flask, swirl, and then add 40 mls concentrated sulfuric acid. Swirl the flask, insert the thermometer, and heat gently so that a temperature of 150° C. is reached in about 1 minute. Swirl continuously during this heating time to prevent local overheating, then remove from heat, and allow to cool to room temperature. Add 200 mls distilled water to the cooled mixture and 5 drops of the ferroin indicator. Titrate with $FeSO_4$ solution in a 50 ml burette from an olive green colour through Kelly green and blue-green to the first muddy brown colour. Note that the addition of the indicator itself does not change the colour of the solution. Note the volume of $FeSO_4$ delivered.

Calculations $$\% \text{ Organics} = \frac{(\text{volume } K_2Cr_2O_7 - N(\text{volume } FeSO_4)) \times 0.2143}{\text{wt. of sludge sample}}$$

where N is the normality of the ferrous solutions determined by titrating 20 mls of $K_2Cr_2O_7$ solution as a blank. The multiplication factor of 0.2143 is broken down as follows:

$$\frac{12}{4000} \times 0.89 \times 0.803 \times 100 = 0.2143$$

where 12/4000 is the millequivalent weight of carbon for the oxidation reaction, the conversion of organics in the oxidation reaction is 89% as reported in the U.S. Dept. of Argiculture Handbook referred to above, and 80.3 is the precent carbon in the butumen sample. It should be noted that the carbon content of bitumen is 80.3% as reflected in the above equation, but the carbon content of soil organic matter is less, being $$58.14\% \left( \frac{1}{1.72} \times 100 \right)$$

which factor is used in the calculation of the referenced method.

The percent observed bitumen is calculated by subtracting the percent adsorbed organics from FIG. 3 (calculated from the methylene blue procedure) from the percent organics (from chromic acid oxidation) calculated as follows:

% adsorbed organics = (% clay minerals) × 0.0234

% observed bitumen = % organics − % absorbed organics

Results

Table 1 gives the data using Ferroin as indicator and compares the percent bitumen to the percent bitumen determined by the conventional solvent extraction (CAM) method. An average for the ratio of the percent bitumen with the titration to the percent bitumen by the CAM method was found to be 0.9571±0.0762 for the Ferroin titration described above.

TABLE 1

COMPARISON OF BITUMEN DETERMINATIONS

| Sample # | Sample Wt. (g) | Volume 1N $K_2Cr_2O_7$ (mls) | Volume 0.506N $Fe(NH_4)_2(SO_4)_2$ (mls) | Volume of $K_2Cr_2O_7$ (mls) | % Organics | % Clay Minerals from Methylene Blue | % Organics Absorbed | % Bitumen | % Bitumen By CAM Method |
|---|---|---|---|---|---|---|---|---|---|
| 1 | 1.72911 | 100 | 35.29 | 82.35 | 10.20 | 14.044 | 0.3286 | 9.87 | 11.2 |
|   | 0.13968 | 20 | 25.86 | 7.07 | 10.84 |   |   | 10.51 |   |
| 2 | 1.38796 | 100 | 65.20 | 67.40 | 10.41 | 14.756 | 0.3453 | 10.06 | 10.3 |
|   | 0.14885 | 20 | 25.55 | 7.22 | 10.40 |   |   | 10.05 |   |
| 3 | 1.47134 | 100 | 74.70 | 62.65 | 9.12 | 17.222 | 0.4030 | 8.72 | 9.3 |
|   | 0.14668 | 20 | 27.25 | 6.37 | 9.31 |   |   | 8.91 |   |
| 4 | 0.22638 | 10 | 4.56 | 7.72 | 7.31 | 18.301 | 0.428 | 6.88 | 8.2 |
| 5 | 0.33558 | 100 | 173.63 | 13.18 | 8.42 | 19.855 | 0.465 | 7.96 | 8.5 |
| 6 | 0.63076 | 100 | 144.13 | 27.93 | 9.49 | 18.136 | 0.424 | 9.07 | 8.1 |
|   | 0.14597 | 10 | 8.55 | 5.72 | 8.41 |   |   | 7.99 |   |
| 7 | 0.98705 | 100 | 114.04 | 42.98 | 9.33 | 17.992 | 0.421 | 8.91 | 8.2 |
|   | 0.17898 | 10 | 5.75 | 7.12 | 8.53 |   |   | 8.11 |   |
| 8 | 1.04207 | 100 | 101.66 | 49.17 | 10.11 | 17.663 | 0.4133 | 9.70 | 9.3 |
|   | 0.18529 | 20 | 23.16 | 8.42 | 9.74 |   |   | 9.33 |   |
| 9 | 1.92485 | 100 | 23.74 | 88.13 | 9.81 | 20.559 | 0.4811 | 9.33 | 10.7 |
|   | 0.23531 | 20 | 16.05 | 11.98 | 10.91 |   |   | 10.43 |   |
| 10 | 0.35956 | 20 | 5.92 | 17.04 | 10.16 | 17.399 | 0.4071 | 9.75 | 10.3 |
| 11 | 0.37313 | 20 | 3.87 | 18.06 | 10.37 | 15.497 | 0.363 | 10.01 | 11.4 |
| C-10 Tailings | 3.40715 | 10 | 17.30 | 0.639 | 0.0402 | 2.03 | 0.0475 | 0.0795 | 0.0065 |

TABLE 1-continued
COMPARISON OF BITUMEN DETERMINATIONS

| Sample # | Sample Wt. (g) | Volume 1N $K_2Cr_2O_7$ (mls) | Volume 0.506N $Fe(NH_4)_2(SO_4)_2$ (mls) | Volume of $K_2Cr_2O_7$ (mls) | % Organics | % Clay Minerals from Methylene Blue | % Organics Absorbed | % Bitumen | % Bitumen By CAM Method |
|---|---|---|---|---|---|---|---|---|---|
| Debitumenized Sludge Sample | 0.46216 | 10 | 13.20 | 2.86 | 1.325 | 22.58 | 0.5283 | 0.797 | 1.30 |

As can be seen from the data in the table the percent bitumen are determined by the method of this invention compares very favorably in sample numbers 1 through 11. In the last two runs it it believed that the very low amount of bitumen in the samples presented as yet unrecognized experimental difficulties which adversely affected the results. Nevertheless, the process of the invention does enable a rapid analysis of bitumen content in tar sands, or tailings and sludge therefrom and thus represents a significant advance in the art.

The invention claimed is:

1. A method for estimating the bitumen content in a material comprised of tar sands tailings or sludge which comprises (1) titrating samples of said materials with methylene blue to an end point showing no further adsorption of said methylene blue and relating said amount of adsorbed methylene blue to clay mineral content from an empirical curve, multiplying said clay mineral content by 0.0234 to obtain the percent adsorbed organic content of said sample, (2) determining the percent of total organic material of said material by a chromic acid oxidation and subtracting the percent adsorbed organics from the percent total organics from the percent total organics to obtain the percent bitumen in said material.

2. The method of claim 1 wherein the percent bitumen content in tar sands tailings is determined.

3. The method of claim 1 wherein the percent bitumen content of sludge is determined.

* * * * *

UNITED STATES PATENT AND TRADEMARK OFFICE
CERTIFICATE OF CORRECTION

PATENT NO. : 4,412,007
DATED : October 25, 1983
INVENTOR(S) : Raymond N. Yong and Amar J. Sethi It is certified that error appears in the above-identified patent and that said Letters Patent are hereby corrected as shown below:

In Claim 1, line 12; delete "from the percent total organics"

Signed and Sealed this

Thirtieth Day of October 1984

[SEAL]

Attest:

GERALD J. MOSSINGHOFF

Attesting Officer

Commissioner of Patents and Trademarks